(12) United States Patent
Raulerson et al.

(10) Patent No.: US 8,454,536 B2
(45) Date of Patent: Jun. 4, 2013

(54) GUIDE WIRE ADVANCER ASSEMBLY AND METHODS FOR ADVANCING A GUIDE WIRE

(75) Inventors: J. Daniel Raulerson, Brewton, AL (US); Timothy M. Schweikert, Levittown, PA (US)

(73) Assignee: Medical Components, Inc., Harleysville, PA (US)

(*) Notice: Subject to any disclaimer, the term of this patent is extended or adjusted under 35 U.S.C. 154(b) by 114 days.

(21) Appl. No.: 12/880,185

(22) Filed: Sep. 13, 2010

(65) Prior Publication Data

US 2010/0331732 A1 Dec. 30, 2010

Related U.S. Application Data

(62) Division of application No. 11/344,616, filed on Feb. 1, 2006, now Pat. No. 7,857,770.

(60) Provisional application No. 60/649,310, filed on Feb. 2, 2005.

(51) Int. Cl.
*A61B 5/00* (2006.01)
*A61M 25/00* (2006.01)

(52) U.S. Cl.
CPC . *A61B 5/00* (2013.01); *A61M 25/00* (2013.01)
USPC ...................................... 600/585; 604/164.13

(58) Field of Classification Search
CPC .................................. A61B 5/00; A61M 25/00
USPC .................... 600/585; 604/164.13
See application file for complete search history.

(56) References Cited

U.S. PATENT DOCUMENTS

| 4,342,313 | A | 8/1982 | Chittenden |
| 4,417,886 | A | 11/1983 | Frankhouser et al. |
| 4,713,059 | A | 12/1987 | Bickelhaupt et al. |
| 4,799,496 | A | 1/1989 | Hargreaves et al. |
| 4,860,757 | A | 8/1989 | Lynch et al. |
| 5,125,905 | A | 6/1992 | Wright et al. |
| 5,125,906 | A | 6/1992 | Fleck |
| 5,263,938 | A | 11/1993 | Orr et al. |
| 5,273,042 | A | 12/1993 | Lynch et al. |

(Continued)

FOREIGN PATENT DOCUMENTS

JP 2004275747 A 10/2004

OTHER PUBLICATIONS

Brief in Opposition dated Aug. 30, 2010; Japanese Patent Application No. 2007-554183 (6 pages).

(Continued)

*Primary Examiner* — Sean Dougherty
(74) *Attorney, Agent, or Firm* — Glenn M. Massina, Esq.; Fox Rothschild LLP (57) ABSTRACT

A guide wire advancer (102) for advancing a guide wire (107) into a patient and including a body having a longitudinal axis. The body includes a first portion (110) adapted to allow a user to advance a guide wire along the longitudinal axis using a finger and a thumb, and a second portion (108) connected to the first portion. The second portion (108) is adapted to allow a user to advance a guide wire (107) along the longitudinal axis using only one finger or the thumb to bias the guide wire against a platform (164) of the second portion when advancing the guide wire (107). Multiple methods of advancing a guide wire using the advancer are also disclosed.

19 Claims, 7 Drawing Sheets

U.S. PATENT DOCUMENTS

| | | | |
|---|---|---|---|
| 5,279,573 | A | 1/1994 | Klosterman |
| 5,282,479 | A | 2/1994 | Havran |
| 5,366,444 | A | 11/1994 | Martin |
| 5,443,081 | A | 8/1995 | Klosterman |
| 5,448,993 | A | 9/1995 | Lynch et al. |
| 5,484,419 | A | 1/1996 | Fleck |
| 5,507,300 | A | 4/1996 | Mukai et al. |
| 5,634,475 | A | 6/1997 | Wolvek |
| 5,810,012 | A | 9/1998 | Lynch et al. |
| 5,843,002 | A | 12/1998 | Pecor et al. |
| 5,851,189 | A | 12/1998 | Forber |
| 6,059,484 | A | 5/2000 | Greive |
| 6,277,100 | B1 | 8/2001 | Raulerson et al. |
| 6,551,281 | B1 | 4/2003 | Raulerson et al. |
| 6,641,563 | B1 | 11/2003 | Vitullo et al. |
| 2004/0082880 | A1 | 4/2004 | Heh et al. |
| 2005/0049572 | A1 | 3/2005 | Schweikert et al. |
| 2005/0245847 | A1 | 11/2005 | Schaeffer |

OTHER PUBLICATIONS

Office Action dated Feb. 9, 2011 of Japanese Patent Application No. JP 2007-554183 (3 pages) (English translation 3 pages).

Drawing No. 5055, "Guidewire Advancer", Oct. 13, 1997, Medical Components, Inc., Harleysville, PA.

Drawing No. 5104, "Guidewire Advancer", Jan. 14, 1997, Medical Components, Inc., Harleysville, PA.

International Search Report, PCT/US06/03522, dated Aug. 22, 2007 (2 pages).

Written opinion, PCT/US06/03522, dated Aug. 22, 2007 (6 pages).

GUIDE WIRE ADVANCER ASSEMBLY AND METHODS FOR ADVANCING A GUIDE WIRE

CROSS REFERENCE TO RELATED APPLICATION

This application is a Divisional application of U.S. Ser. No. 11/344,616 filed Feb. 1, 2006, which in turn claims priority from U.S. Provisional Patent Application Ser. No. 60/649,310 filed Feb. 2, 2005.

FIELD OF THE INVENTION

The invention relates to medical devices and more particularly to guide wire advancers.

BACKGROUND OF THE INVENTION

Catheters may be used for introducing and removing fluids in and from various vessels and cavities throughout the body. Central venous catheters, for example, are generally placed in four common locations within the chest and/or in the femoral vessels. They may be placed, for example, in either the right or left subclavian vein or in the right or left internal jugular vein. Such catheters use a guide wire to properly place the catheter in the catheterized area.

Using landmarks, vessels are identified and may be cannulated by first aspirating the vessel with a long hollow needle, which may be attached to a syringe or other aspirating device to ensure that the vessel has been properly located. When the vessel has been properly located and aspirated, if a syringe is used, the syringe is disconnected and a thin guide wire is passed through the needle into the hollow passage, or lumen, of the vessel. Other introducers allow the guide wire to pass through the syringe or device without removing the device from the needle. The needle or other introducer device is then removed, leaving one end of the guide wire within the vessel. The other end of the guide wire projects beyond the surface of the skin.

At this point, the simplest method of catheter placement is to pass a catheter into the vessel directly over the guide wire. The guide wire is then removed, leaving the catheter in position within the vessel. The catheter as placed can then function in various applications such as infusion, perfusion, hemodialysis and the like.

The guide wires used for such procedures are generally spring wires, which typically have a curved J-shaped tip. The nature of the spring wire, which is typically constructed from a memory alloy, causes the tip to return to the J-shape after applied stress is removed. Therefore, in order to slide the tip through the device and to keep the wire from bending back on itself while entering the patient, such wires are typically introduced through a straightening device. The guide wire has a relatively long length. For convenience, the wire is typically packaged and used as a coil. The coils generally have plastic clips which help to hold the coil together for handling. In addition, the coils can be packaged in protective storage tubes which also may use clips to hold the tubes in a coiled configuration.

The mechanical difficulties encountered by a physician or other medical personnel using such guide wires typically are the result of the need to use two hands to handle the guide wire and to operate an advancing apparatus while inserting the guide wire through the needle into the patient. Various prior art devices are directed to simplifying the advancing and insertion procedure, including a plastic cone having a hole at the tip of the cone for passing the guide wire through the hole into the introducer hub, and a shuttling device as described in U.S. Pat. No. 4,713,059. These devices, while assisting in advancing the wire through the introducer and guiding the wire into the needle, require two hands to operate.

Guide wires typically range in diameter from a relatively large 0.045 in to a relatively very small 0.018 in. Difficulty is usually encountered in controllably inserting the distal tip of at least the very small diameter size guide wire into the proximal opening of the introducer or syringe or proximal catheter fitting for vascular insertion into the patient.

Other solutions to the problem of two-handed guide wire advancing and straightening include a device as described in U.S. Pat. No. 5,125,906, which teaches a trigger-like handle with a clip which can be attached to a guide wire feeding tube or coil. The device has a frustoconical, tapered, distal end portion. The device is held with the fingers coiled around the trigger handle and the guide wire is fed into the device through a proximal opening, slid across a flat surface by the thumb and through the distal end portion into a syringe or needle introducer. A modified version of the device is disclosed in U.S. Pat. No. 5,484,419, which includes an additional, separate conical end fitting which can be placed over the end portion to help feed the guide wire into the needle and which has an arched underneath surface for facilitating handling of the device to enhance sliding of the guide wire over a flat top surface of the device. One problem with these guide wire advancers is the inability of the physician to accurately determine whether and how far the guide wire is advancing into the vessel using the thumb alone.

A virtually identical device is described in U.S. Pat. No. 5,507,300, which provides a rubber band along the wire guide to allow the physician to stop the insertion of the guide wire without letting the guide wire slip along the guide.

U.S. Pat. No. 5,366,444 discloses a guide wire advancer which provides a head with a guide opening, a discharge opening, and an open platform therebetween. A guide wire is advanced over the platform with a thumb, with a forefinger engaging a depression on an underside of the platform.

Other devices disclosed by U.S. Pat. Nos. 4,860,757, 4,917,094, 5,273,042, 5,438,993, and 5,448,993 describe a guide wire housed in a tube with apertures or a conical straightener as described above with a thumb opening cut into the conical portion. A physician's thumb fits into the aperture to engage the guide wire to advance or retract the guide wire through the tube.

A device disclosed by U.S. Pat. No. 6,551,281, invented by the present inventor, describes a guide wire advancer with an open central portion that flexibly connects a proximal portion and a distal portion through which a guide wire is contained. A physician grasps the guide wire between thumb and forefinger at the central portion and feeds the guide wire through the distal portion. Alternatively, while grasping the guide wire between the thumb and forefinger as described above, the physician advances the guide wire distally, compressing the open central portion by disposing the proximal portion toward the distal portion. Upon release of the guide wire and the advancer, the open central portion reverts to its original shape. Friction between the guide wire and the blood vessel into which the guide wire has been inserted keeps the guide wire from being pulled out of the vessel.

The above-described guide wire straighteners allow guide wires to be inserted in limited ways. However, different physicians have different preferences on techniques to be employed to advance a guide wire. Each of the guide wire advancers described above may require a physician to insert a guide wire using a technique or method with which he or she is uncomfortable or unfamiliar, risking potential injury to the patient during insertion.

Therefore, there is a need in the art for a guide wire advancer and/or straightening device which is alternatively operable through at least one of several alternate methods so that the physician inserting the guide wire has the option of using the method with which he or she is most comfortable using.

SUMMARY OF THE INVENTION

The present invention is a guide wire advancer including a body having a longitudinal axis and having a first advancer portion adapted to enable a first advancing technique, and at least a second advancer portion adapted to enable at least a second advancing technique. The first portion is adapted to allow a user to advance a guide wire along the longitudinal axis using a finger and a thumb to directly frictionally engage the wire, by providing a large opening exposing the guide wire as it extends across the large opening. The second portion is adapted to allow a user to advance a guide wire along the longitudinal axis using only one finger or the thumb to bias the guide wire against a platform of the second portion when advancing the guide wire. The more distal of the first and second portions includes a distal tip portion that is preferably frustoconical. Optionally, the first and second portions may be independently rotatable about the longitudinal axis.

Preferably, the first portion comprises distal and proximal portions that define aligned first and second passageways therethrough through which the guide wire extends and is advanced. Also, preferably, the first portion comprises a central portion having first and second members extending between the distal and proximal portions, with the first and second members diverging and then converging, thus defining the large opening therebetween. The first and second members may be flexible and may be manually deformed to urge the proximal portion toward the distal portion to advance the guide wire, with the practitioner holding the proximal and distal portions, and providing a third optional advancing technique.

The guide wire advancer thus provides three optional advancing techniques by the practitioner. The practitioner also may use more than one of the techniques sequentially at his or her discretion. The method of the present invention includes providing a guide wire advancer having the first and second portions set forth hereinabove, and selecting one or more of the plurality of optional techniques to advance the guide wire.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Certain terminology is used in the following description for convenience only and is not limiting. The words "distal" and "proximal" respectively designate directions in the drawings toward and away from the insertion end of the device. The terminology includes the words above specifically mentioned, derivatives thereof and words of similar import.

Figure 1:
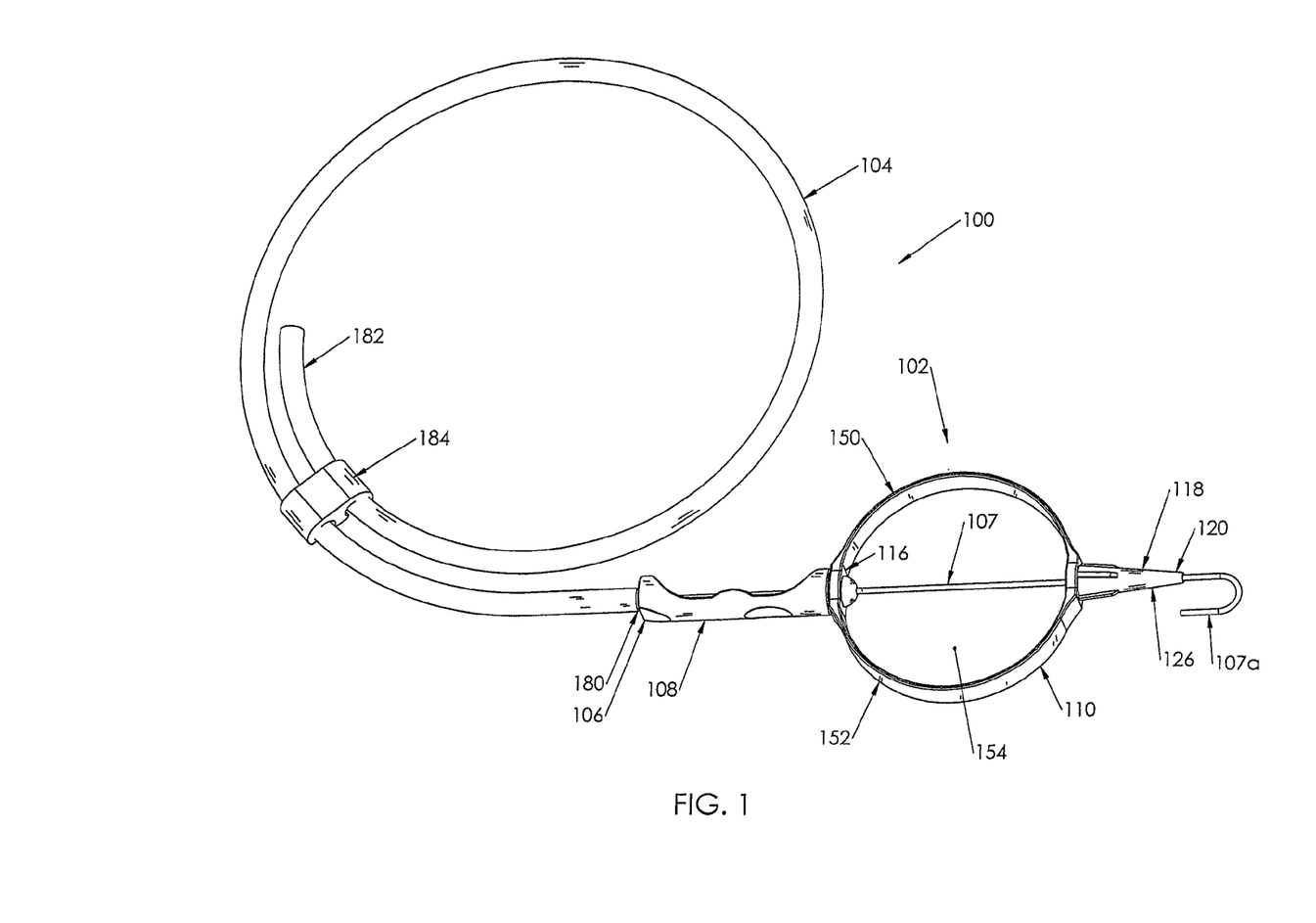
FIG. 1 is a perspective view of a guide wire advancer assembly in accordance with the present invention.
Figure 2:
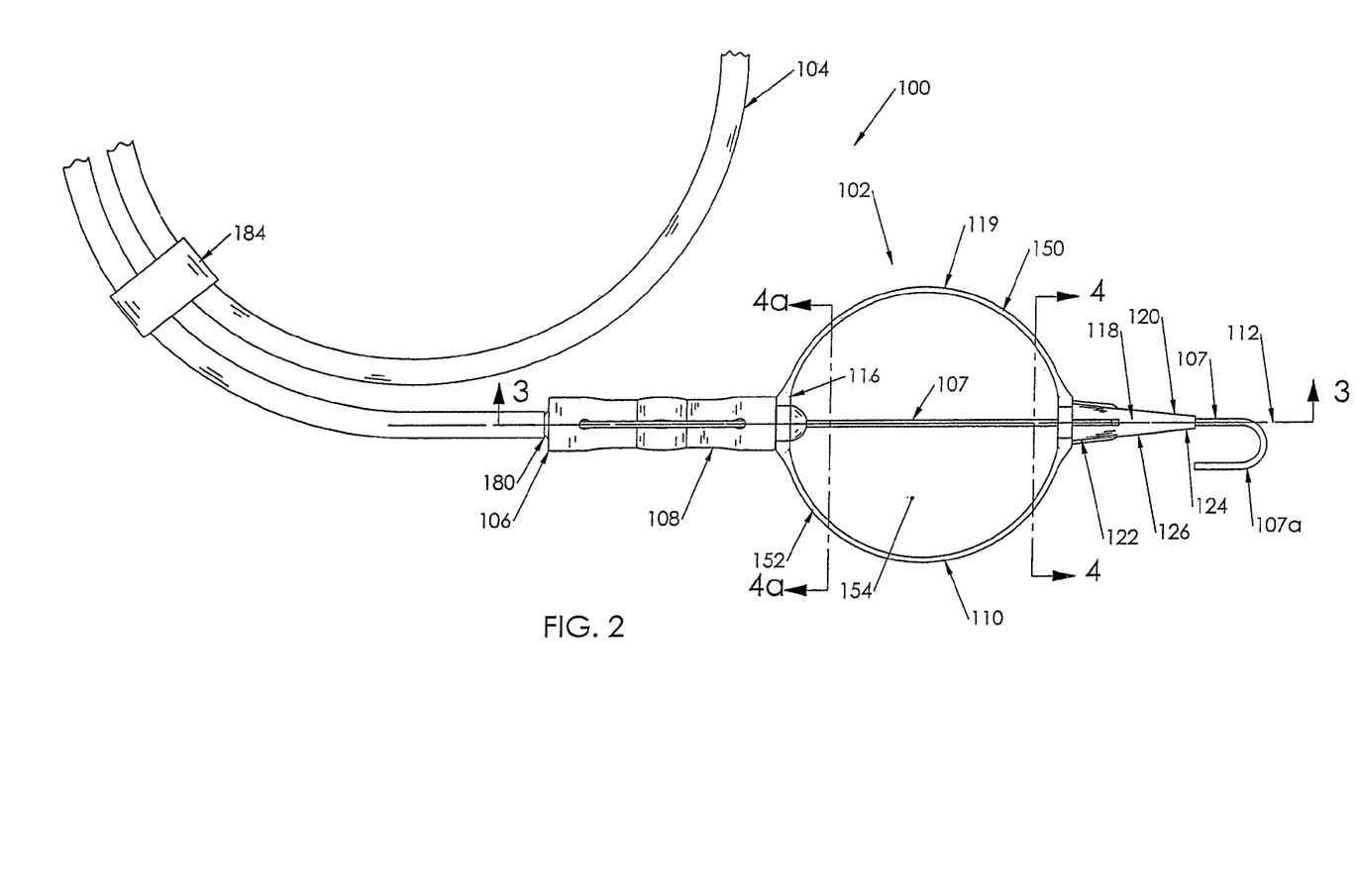
FIG. 2 is a top plan view of the guide wire advancer assembly of FIG. 1.

Referring to the drawings in detail, there is shown in FIGS. 1 and 2 a guide wire advancer assembly, generally designated as 100, and a guide wire advancer, generally designated as 102, according to one preferred embodiment of the present invention. The assembly 100 includes the advancer 102 and a guide wire storage tube 104, which is connected to a proximal end 106 of the advancer 102. A guide wire 107 is stored in the tube 104 and extends through the advancer 102 for insertion into a blood vessel; while the guide wire remains at least partially disposed within the tube at the proximal end of the guide wire, minimizing the risk of contamination.

The advancer 102 is comprised of a body having a proximal portion 108 and a distal portion 110. A longitudinal axis 112 extends through the advancer 102, co-linear with the portion of the guide wire 107 that extends through the advancer 102.

Figure 3:
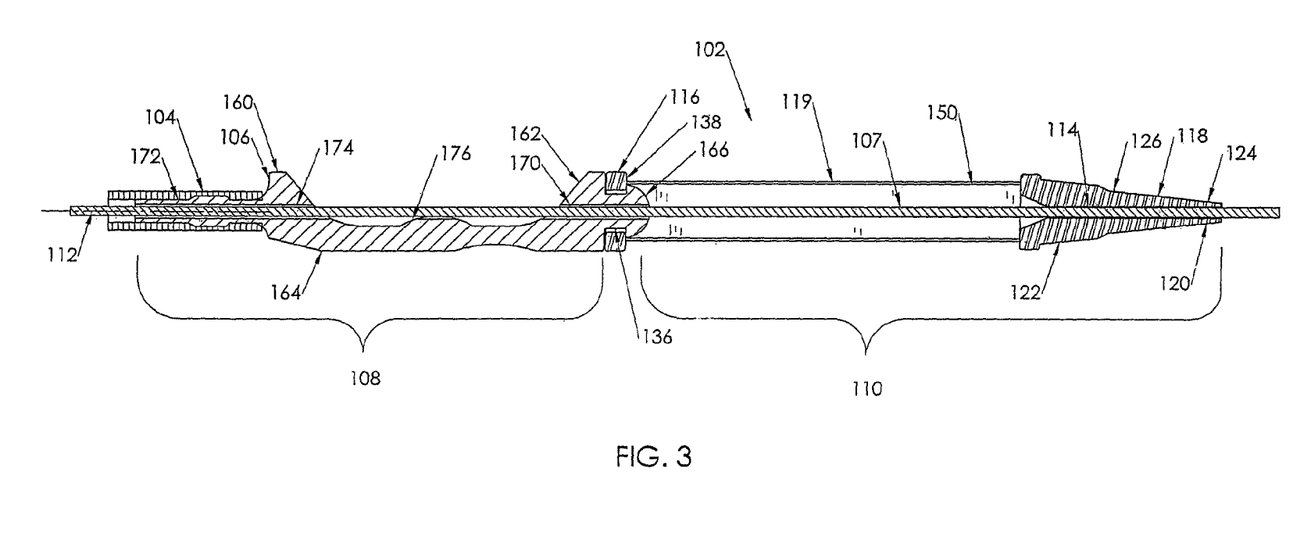
FIG. 3 is a cross-sectional view of the guide wire advancer assembly taken along line 3-3 of FIG. 2.

Referring now to FIG. 3, the distal portion 110 includes a passageway 114 which extends longitudinally therethrough, preferably along the longitudinal axis 112. The diameter of the passageway 114 is preferably sized to receive the guide wire 107 therein. Preferably, for different gauge guide wires, the diameter of the passageway 114 and the associated advancer 102 can be larger or smaller with respect to the size of the guide wire 107 to be used. The diameter of the passageway 114 should be sized such that the guide wire 107 fits through snugly, with minimal clearance between the outer diameter of the guide wire 107 and the diameter of the passageway 114 of the distal portion 110, but not so tightly as to inhibit advancement of the guide wire 107 through the passageway 114. Preferably, the guide wire 107 should substantially fill a lumen to minimize blood loss through a separate introducer such as an introducer device (not part of the present invention) but should still be able to be advanced smoothly through the lumen in the introducer device and into a patient without too much effort on the part of the physician or other medical personnel using the advancer assembly 100.

The introducer device used can vary and many are known in the art. The introducer device may be a conventional introducer or the advancer may be used to feed directly into a catheter and/or catheter fitting which can itself serve as an introducer. As such, "introducer device" as used herein includes any intervening device between the advancer 102 and the patient's vessel or cavity for receiving the guide wire 107. For example, the introducer device may be a needle having a proximal coupling or other fitting which remains distally inserted in a patient after disconnect of an aspirating syringe, or an apparatus such as a catheter introducer syringe which has a needle end inserted in the patient and a syringe body or other proximal attachment connected to the needle. Alternatively, the introducer device may be a RAULERSON ONE-STEP™ introducer bulb sold by Medical Components, Inc. of Harleysville, Pa. (not shown), as disclosed in U.S. Pat. No. 6,277,100. When such syringes, or similar devices, are used as the introducer device, the proximal opening for inserting the advancer 102 would generally be located on the proximal end of the syringe body or other proximal needle attachment. If the introducer device is a needle, the opening for inserting the tip 120 of the advancer 102 would be the coupling or other proximal end fitting on the needle after the aspirating syringe has been removed.

Referring still to FIG. 3, the distal portion 110 of the advancer 102 includes a proximal end 116, a distal end 118, and a central portion 119 that extends between the proximal end 116 and the distal end 118. The distal end 118 includes a tip 120 which may have any suitable shape. Preferably, the tip 120 is configured to fit within a fitting on the proximal end of an introducer such as the introducer device described above. The tip 120 is preferably conical, but may be also be cylindrical along its length or cylindrical along only a portion of its length with a graduated shape such as a smaller diameter cylindrical portion or an end portion which is tapered or conical. Preferably, the tip 120 tapers down from a proximal end 122 to a distal end 124. A bullet-shaped end may also be used wherein the cross-section in the longitudinal direction would appear parabolic. The shape may vary; however, it is preferred that the tip 120 mate with the type of introducer selected. The actual shape of the tip 120 should be determined by a number of factors, including but not limited to, ease of insertion and the shape of the passageway through a fitting into a proximal end of the introducer device into which the tip 120 is to be inserted.

The tip 120 further has an exterior surface 126 which may be smooth or rough. While not preferred, longitudinally extending gripping ribs (not shown) can be provided to extend along the surface 126 of the tip 120, particularly if the tip 120 is cylindrically shaped, or along a portion of the surface 126 of the tip 120. The exterior surface 126 of the tip 120 is preferably adapted to mate with an interior surface of the introducer device. For example, if the lumen in the proximal end of the introducer device were conically shaped, the exterior surface 126 of the tip 120 may be conically configured to more smoothly enter the lumen and to mate more securely with the introducer device.

Figure 4:
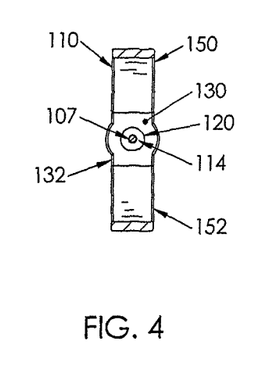
FIG. 4 is a cross-sectional view of the advancer taken along line 4-4 of FIG. 2.

With reference to FIGS. 3 and 4, the distal portion 110 preferably has a generally rectangularly shaped portion 130 attached to the tip 120. The generally rectangularly shaped portion 130, as well as the entire distal portion 110, is preferably integrally molded as one piece. The generally rectangularly shaped portion 130 preferably extends transversely across the advancer 102 and has an inner surface 132 which faces the central portion 119. The passageway 114 terminates at the surface 132. When passing the guide wire 107 through the advancer 102 in a direction from the proximal end 116 to the distal end 118, the guide wire 107 would enter the distal end 118 through the terminal end of the passageway 114 at the surface 132.

Figure 4A:
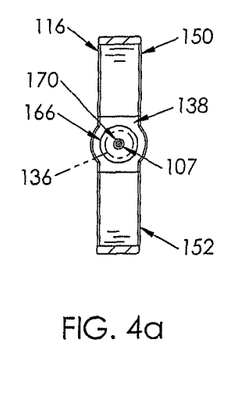
FIG. 4a is a cross-sectional view of the advancer taken along line 4a-4a of FIG. 2.

Referring back to FIG. 3, the proximal end 116 of the advancer 102 has a passage 136 which extends longitudinally through the proximal end 116, which is sized to receive the guide wire 107 to facilitate insertion of the guide wire 107 through the advancer 102. In the embodiment shown, the passage 136 is axially aligned with the passageway 114 through the distal end 118, generally along the central longitudinal axis 112. While such alignment is not necessary for the invention, it is preferred for ease of manufacture and to facilitate advancing of the guide wire 107 through the advancer 102. The proximal end 116 preferably has an inner end surface 138, shown in FIGS. 3 and 4a, which faces, but is spaced from, the inner surface 132 of the distal end 118.

Now referring back to FIG. 2, the central portion 119 of the advancer 102 includes a pair of first and second longitudinally extending, preferably curved connecting members 150, 152, which interconnect the proximal and distal ends 116, 118. Preferably, the connecting members 150, 152 are flexible, for reasons that will be explained. The central portion 119 may be transversely spaced from and on opposing sides of the passageways 136, 114 through the proximal and distal ends 116, 118, respectively, and extend between the proximal end 116 and the distal end 118. Each connecting member 150, 152 is preferably generally arcuate such that an interior curved surface of each connecting member 150, 152 faces the central longitudinal axis 112. However, other shapes besides arcuate are envisioned and may be used within the scope of the invention. Such other shapes can include polygonal such as quadrilateral, hexagonal, octagonal as well as others not mentioned herein. The central portion 119 includes an opening 154 defined by a space between the curved surfaces of the connecting members 150, 152 for advancing the guide wire 107 through the advancer 102.

The opening 154 preferably provides access for the user to manipulate and advance the guide wire 107, preferably by gripping the wire 107 between a thumb and forefinger and feeding the wire 107 in a controllable manner. It is important is that the opening 154 between the members 150, 152 be configured to be sufficiently large so as to provide access to the physician to grip the guide wire 107 with the thumb and forefinger through the opening 154 at the central portion 119 to advance the guide wire 107 through the advancer 102.

Figure 3A:
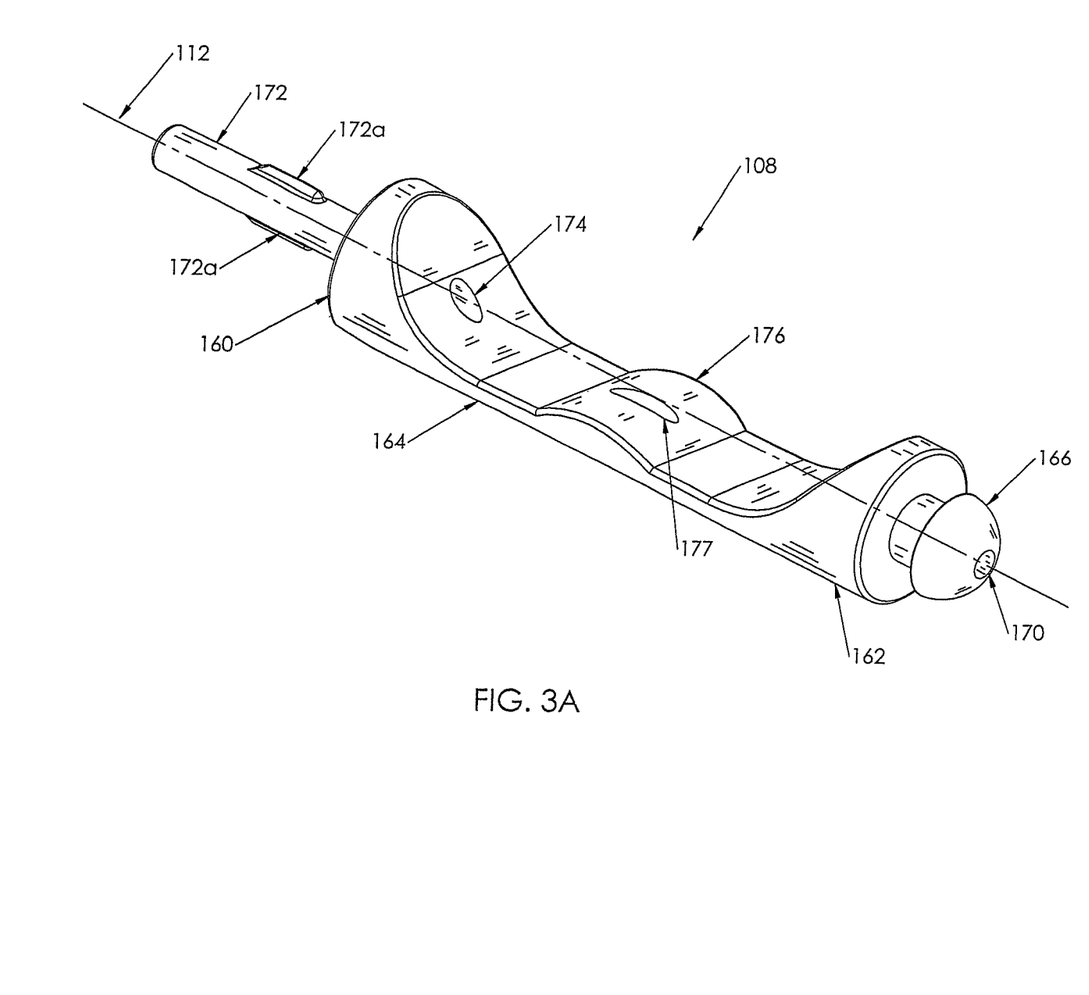
FIG. 3A is a perspective view of a proximal portion of the advancer of FIG. 1.

The proximal portion 108 is shown in an enlarged perspective view of FIG. 3A. The proximal portion 108 includes a proximal end 160 and a distal end 162. A generally planar portion 164 extends between the proximal end 160 and the distal end 162. The distal end 162 of the proximal portion 108 includes a bulbous connector knob 166 extending along the longitudinal axis 112 to rotatably connect the proximal portion 108 and the distal portion 110 to each other (shown in FIG. 3), so that the proximal portion 108 and the distal portion 110 are able to rotate relative to each other about the longitudinal axis 112. The connector knob 166 extends through the passage 136 in the distal portion 110. During assembly of the advancer 102, the connector knob 166 is force fit through the passage 136 from the proximal end of the passage 136 to the distal end of the passage 136 so that the connector knob 166 extends into the opening 154.

The distal end 162 also includes a distal passageway 170 extending along the longitudinal axis 112. The distal passageway 170 is sized to allow the guide wire 107 to slide easily through during guide wire insertion into the patient.

The proximal end 160 includes a male fitting 172 extending along the longitudinal axis 112. The male fitting 172 is configured to fit into an open end of the guide wire storage tube 104 (FIGS. 1 and 2) and to engage the storage tube 104 with an interference fit so that the storage tube 104 will not slip from the proximal end 160. However, the fit between the storage tube 104 and the proximal end 160 should be loose enough to allow the storage tube 104 to easily rotate about the longitudinal axis 112, allowing the plane of the storage tube 104, as shown by the plane of the paper in FIG. 2, to rotate to facilitate handling by the physician during use. The male fitting 172 may be varied for different sized tubes. The male fitting 172 may also include a plurality of nubs 172a that extend away from the longitudinal axis 112 to further provide gripping strength to retain the male fitting 172 within the storage tube 104.

The proximal end 160 also includes a proximal passageway 174 extending along the longitudinal axis 112. The proximal passageway 174 is sized to allow the guide wire 107 to slide easily through during guide wire insertion into the patient.

The generally planar portion 164 extends below the longitudinal axis 112, as shown in FIG. 3A. The generally planar portion 164 includes a raised convex portion 176 that extends from the generally planar portion toward the longitudinal axis 112. The raised convex portion 176 may optionally include a shallow generally oblong cutout 177 that extends generally along the longitudinal axis 112 to ensure that the guide wire 107 enjoys relatively free movement along the convex portion 176. It can be seen in FIGS. 3 and 6 that the guide wire protrudes slightly above the shallow cutout.

In the preferred embodiment, the invention further comprises an assembly 100 for feeding and straightening the guide wire 107 as shown in FIGS. 1 and 2. The assembly 100 includes the advancer 102 connected to the guide wire storage tube 104. The guide wire 107 is enclosed within the storage tube 104, and the storage tube 104 can easily be held in place while the guide wire 107 is advanced forward into the patient. The storage tube 104 is preferably a flexible plastic tube which may be formed of any suitable polymeric material. Such tubes are well known in the art and are commercially available. The tube 104 has an open distal end 180 which connects to the proximal portion 108 of the advancer 102, preferably by coupling with the male fitting 172. The storage tube 104 may have one or more securing clips 184 which are typically sold with packaged storage tube coils. Such securing clips 184 help to retain the storage tube 104 in a coiled condition as seen in FIGS. 1 and 2. The guide wire 107 extends longitudinally, and preferably loosely, within the storage tube 104. The proximal end 182 of the storage tube 104 may be equipped with couplings or a sealing cap (not shown) for preventing the guide wire 107 from advancing in the proximal direction out the proximal end 182 of the storage tube 104. While a storage tube 104 is preferred, a bare coil of guide wire 107 may also be inserted directly into the proximal portion 108 of the advancer 102 without any structure directing the wire 107 into the advancer 102. However, the guide wire storage tube 104 improves handling of the coiled guide wire 107 and helps to prevent contamination and to maintain the guide wire 107 in a sterile condition. When the guide wire 107 is fully within the advancer 102 such that the guide wire 107 extends through the distal portion 114 from the storage tube 104, the guide wire 107 preferably extends across the central portion 119 such that the guide wire 107 generally extends along the longitudinal axis 112.

The advancer 102 of the present invention may be made of any suitable material preferably capable of being sterilized, such as metals, metal alloys, polymeric and/or elastomeric materials. The material need not be biocompatible as the advancer 102 itself is not designed to enter the patient. In the preferred embodiment, for manufacturing economy and simplicity, the advancer 102 is made of a heat moldable or thermoformable polymeric or elastomeric material. The preferred polymeric materials include thermoplastic or thermosetting polymers and copolymers, and more preferably, thermoplastic polymers which are capable of being injection molded or extruded. In the preferred embodiment, the proximal and distal portions 108, 110 of the advancer 102 are individually formed by injection molding using a mold having the desired configuration and using a rod or other means to maintain the longitudinally extending passageways 114, 136, 170, 174 through the distal and proximal portions 110, 108. In the preferred embodiment, the advancer 102 is formed of polyethylene, and even more preferably, polypropylene such as PP BSL PF 511 NT PROFAX® polypropylene sold by General Polymers. It is also within the scope of the invention to use reinforced polymeric or elastomeric or composite materials for forming the advancer with long or short fibrous reinforcements such as glass, carbon fiber, or polymeric fibers, fillers, or metal inserts or metallic wire mesh as well as any other suitable polymeric molding reinforcement. Pigments or other coloring agents may be added to the molding polymer to provide a bright or distinctive color to the advancer 102 for good visual identification during the guide wire insertion procedure.

The dimensions of the advancer 102 should be relatively small and sized to fit easily within the user's fingers while allowing a sufficiently long and wide central portion 119 for achieving adequate gripping and feeding movement using the thumb and preferably the forefinger. The size and shape of the opening 154, within the parameters as discussed above, should allow thumb and forefinger access to, and movement of the particular guide wire 107 through, the advancer 102. The tip 120 can similarly be sized for fitting easily into the proximal end of the guide wire introducer device for directing the guide wire 107 from the advancer 102 into the patient. Preferably, the overall length of the advancer 102 from the distal end of the tip 120 to the proximal end 160 of the proximal portion 108 is about 100 mm.

The wire 107 should advance through with an easy advancing motion, but should not interfere with the physician feeling any obstruction within the patient during the feeding operation as described further below. Preferably, some tactile control between the wire 107 and the physician's thumb and forefinger is preferred. Preferably, a distal tip 107a of the guide wire 107 is curved, as shown in FIGS. 1 and 2. The tip 107a is curved to prevent the tip 107a from catching and perforating the vessel as the guide wire 107 is being passed through the lumen of a vessel in the patient P (see FIG. 5).

While the preferred embodiment of the guide wire advancer 102 disclosed above includes the proximal portion 108 disposed proximally of the distal portion 110, those skilled in the art will recognize that the portions may be rearranged such that the proximal portion 108 is disposed distally of the distal portion 110, without departing from the scope and intent of the present invention.

The present invention further includes a method for advancing and straightening the guide wire 107 for insertion into the patient, preferably using an apparatus such as the advancer assembly 100 as described above. However, those skilled in the art will realize that the advancer 102 can be used alone, without the storage tube 104. Typically, the vessel to be catheterized is located and cannulated by aspirating the vessel with the introducer device. After the vessel is aspirated, guide wire 107 is inserted into the vessel through the lumen of the introducer device according to one of the methods described below.

Figure 5:
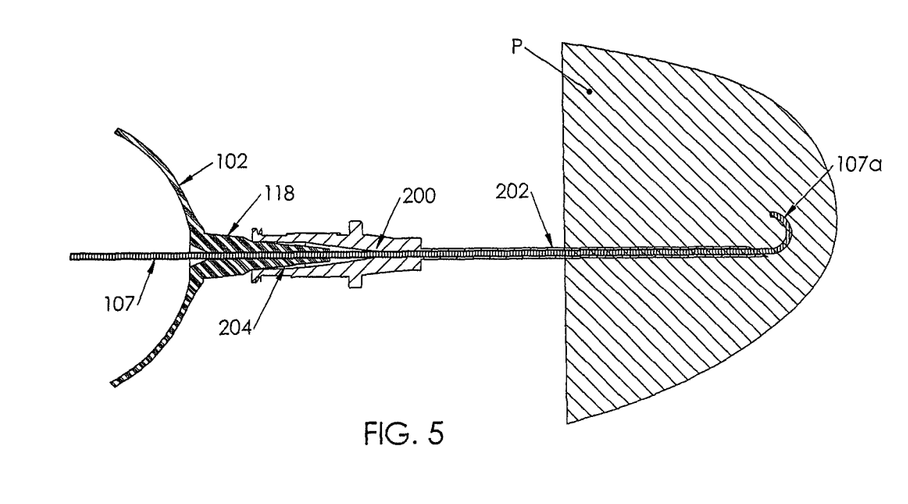
FIG. 5 is a cross-sectional view of a portion of the advancer assembly of FIG. 1 inserted into an introducer needle which has been inserted into a patient.

FIG. 5 shows the advancer 102 having been inserted in the proximal end of an introducer device 200. The introducer device 200 generally includes a lumen 202 connected to a luer lock connector 204, which has been disconnected from a mating fitting on an aspirating syringe (not shown).

Figure 6:
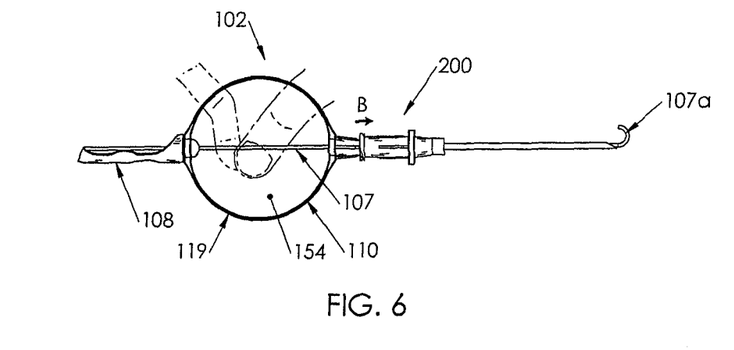
FIG. 6 is a side elevational view showing a user manipulating a guide wire using the guide wire advancer assembly according to a first method of using the present invention.

Referring to FIGS. 5 and 6, it is preferred that the introducer 102 be held along the central portion 119. Using one hand, the user's thumb and finger, preferably forefinger, are preferably used for the manipulation and feeding of the guide wire 107 through the central portion 119. Using the other hand, the user preferably holds on to the introducer device 200 to steady the introducer device 200. According to one preferred method, the tip 120 of the advancer 102 is inserted into the proximal end of the introducer device 200, which has already been inserted into the patient, as shown in FIG. 5. Preferably the advancer 102 or the assembly 100 having the storage tube 104 and guide wire 107 as described in detail above, are used in the preferred method. The curved distal end 107a of the guide wire 107 is already extended from the distal end 118 of the distal portion 110 and must be straightened prior to being inserted into the lumen 202 of the introducer device 200. Such straightening is accomplished simply by manually moving the guide wire proximally such that the J-shaped tip is withdrawn into the tip 120 of the advancer and becomes straight within the tip, as is known to be done with prior art advancers. Once the tip 107a is inserted into the lumen 202, the user uses his or her thumb and finger, preferably the forefinger, to grasp and controllably feed the wire 107. The wire 107 is thus moved through the central portion 154, and pushed through and out of the advancer 102 in the direction of arrow "B" in FIG. 6.

Figure 7:
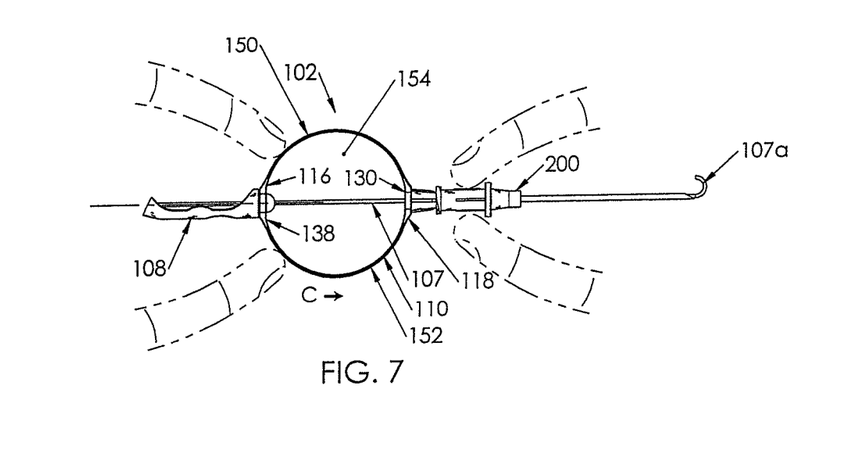
FIG. 7 is a side elevational view showing a user manipulating a guide wire using the guide wire advancer assembly according to a second method of using the present invention.

In an alternately preferred method, shown in FIG. 7, the user grasps the guide wire 107 and the advancer 102 in one hand, the introducer device 200 in the other hand, and compresses the opening 154 in the advancer 102 such that the inner end surface 138 of the proximal end 116 is advanced toward the inner end surface 130 of the distal end 118 in the direction of arrow "C" in FIG. 7. The connecting members 150, 152, because of their flexibility, easily deform to allow such movement. As the advancer 102 is compressed, the guide wire 107 is advanced into the patient. The physician then releases the guide wire 107 and the advancer 102. The guide wire 107, due to friction between the guide wire 107 and the patient, remains in place and the advancer 102, due to the flexibility of the connecting members 150, 152, returns to the uncompressed position. The physician can repeat the process until the guide wire 107 is advanced a desired length.

Figure 8:
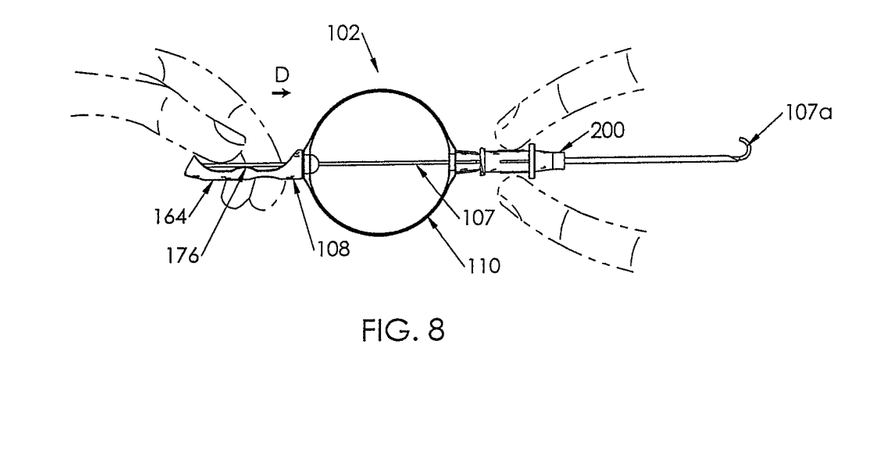
FIG. 8 is a side elevational view showing a user manipulating a guide wire using the guide wire advancer assembly according to a third method of using the present invention.

In another alternatively preferred method, shown in FIG. 8, the user grasps the introducer device 200 with one hand, and grasps the proximal portion 108 of the advancer 102 with the other hand. The user depresses the guide wire 107 against the convex portion 176 of the generally planar portion 164, preferably with the thumb, and urges the guide wire 107 distally along the longitudinal axis, as shown by the arrow "D" in FIG. 8, so that the guide wire 107 advances into the introducer device 200. The user then removes his/her thumb from the guide wire 107 and repeats the process until the guide wire 107 is advanced a desired length.

In all three preferred methods disclosed above, as the guide wire 107 is advanced, the guide wire end 107a passes out the end of the introducer device 200. The introducer device 200 is typically already within a vessel or other area to be catheterized in a patient (not shown) which will further hold the end 107a of the guide wire 107 straight when the end 107a of the guide wire 107 passes distally out of the introducer device 200. Therefore, when the end 107a of the guide wire 107 passes through the distal end of the introducer device 200, the end 107a is still straight and may pass directly into the patient in the area to be catheterized such as a blood vessel, a body cavity, or other area to be catheterized. The introducer device keeps the tip 107a of the guide wire 107 straight until the tip 107a exits the distal end of the introducer device 200 in the patient's body where the tip 107a can curl back to its natural, curved position.

According to any of the above-described methods, once the guide wire 107 is properly located within the patient, the storage tube 104, the advancer 102, and the introducer device 200 may each be removed from the proximal end of the guide wire 107. The introducer device 200 may in some cases be retained on the patient depending upon the procedure. The guide wire 107 is retained in the patient with the distal end 107a in the area to be catheterized, and the proximal end outside the patient. The catheter or other cannula is introduced into the patient by passing a catheter over the guide wire 107 in accordance with standard medical procedures.

Preferably, the apparatus used in the present method is the advancer 102 or the assembly 100. However, it should be understood, based on this disclosure, that other similar advancing devices having suitable tips and exterior gripping surfaces which are capable of carrying out the steps of the preferred method as described herein and allowing access to the thumb and a finger for controllably advancing the guide wire 107 by feeding may be used.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A guide wire advancer comprising:
   an advancer body comprising:
      a distal portion including a first distal end portion defining a first passageway extending longitudinally through the first distal end portion, a first proximal end portion defining a second passageway extending longitudinally through the first proximal end portion, and a central portion having first and second connecting members extending between the first distal end portion and the first proximal end portion, wherein the first and second connecting members define an opening; and
      a proximal portion connected to the distal portion and including an axially extending guide wire platform extending between a second distal end portion defining a third passageway extending longitudinally through the second distal end portion and a second proximal end portion defining a fourth passageway extending longitudinally through the second proximal end portion with a longitudinal axis extending through the third and fourth passageways and at least one of the first and second passageways,
   wherein the distal portion is disposed distally of the proximal portion.

2. The guide wire advancer according to claim 1, wherein the distal portion and the proximal portion are rotatable relative to one another about the longitudinal axis.

3. The guide wire advancer according to claim 1, wherein the first distal end portion concludes in an axially extending distal tip.

4. The guide wire advancer according to claim 3, wherein the distal tip is frustoconical.

5. The guide wire advancer according to claim 1, wherein at least one of the passageways is adapted to frictionally engage a guide wire passing therethrough.

6. The guide wire advancer according to claim 1, wherein the first and second connecting members are arcuate.

7. The guide wire advancer according to claim 1, wherein the opening is sufficiently large to enable the finger and the thumb of a user to grasp a guide wire extending through the opening and advance the guide wire along the first and second passageways.

8. The guide wire advancer according to claim 1, wherein the guide wire platform defines an open generally planar portion extending parallel to the longitudinal axis.

9. The guide wire advancer according to claim 1, wherein the distal portion is disposed proximally of the proximal portion.

10. A guide wire advancer comprising:
an advancer body comprising:
a distal portion including a first distal end portion defining a first passageway extending longitudinally through the first distal end portion, a first proximal end portion defining a second passageway extending longitudinally through the first proximal end portion, and a central portion having first and second connecting members extending between the first distal end portion and the first proximal end portion, wherein the first and second connecting members define an opening; and
a proximal portion connected to the distal portion and including an axially extending guide wire platform extending between a second distal end portion defining a third passageway extending longitudinally through the second distal end portion and a second proximal end portion defining a fourth passageway extending longitudinally through the second proximal end portion with a longitudinal axis extending through the third and fourth passageways and at least one of the first and second passageways, wherein the platform includes a raised convex portion having a shallow cutout across the raised convex portion aligned with the longitudinal axis.

11. The guide wire advancer according to claim 1, wherein the platform defines a support surface parallel to and spaced from the longitudinal axis.

12. A guide wire advancer comprising:
an advancer body comprising:
a distal portion including a first distal end portion defining a first passageway extending longitudinally through the first distal end portion, a first proximal end portion defining a second passageway extending longitudinally through the first proximal end portion, and a central portion having first and second connecting members extending between the first distal end portion and the first proximal end portion, wherein the first and second connecting members define an opening; and
a proximal portion connected to the distal portion and including an axially extending guide wire platform extending between a second distal end portion defining a third passageway extending longitudinally through the second distal end portion and a second proximal end portion defining a fourth passageway extending longitudinally through the second proximal end portion with a longitudinal axis extending through the third and fourth passageways and at least one of the first and second passageways, wherein the distal and proximal portions are connected at the first proximal end portion and the second distal end portion.

13. The guide wire advancer according to claim 12, wherein the second distal end portion defines a connector knob which is received in the second passageway to connect the distal and proximal portions.

14. The guide wire advancer according to claim 13, wherein the third passageway extends through the connector knob.

15. The guide wire advancer according to claim 13, wherein the connector knob and second passageway are configured to define a rotatable connection between the distal and proximal portions.

16. The guide wire advancer according to claim 12, wherein one of the first distal end portion and second proximal end portion concludes in an axially extending distal tip with the respective passageway extending through the distal tip.

17. The guide wire advancer according to claim 16, wherein the first distal end portion concludes in the distal tip and the second proximal end portion concludes in a fitting configured for connection to a guide wire storage tube.

18. The guide wire advancer according to claim 17, wherein the fourth passageway extends through the fitting.

19. The guide wire advancer according to claim 12, wherein one of the first and fourth passageways has an inner diameter which is smaller than inner diameters of the second and third passageways and the other of the first and fourth passageways.

* * * * *